United States Patent [19]

Howard, Jr. et al.

[11] Patent Number: 5,262,317

[45] Date of Patent: Nov. 16, 1993

[54] POLYACRYLONITRILE MODIFIED WITH HYDROGEN HALIDE FOR IMMOBILIZATION OF BIOLOGICAL SUBSTANCES

[75] Inventors: Edward G. Howard, Jr., Hockessin, Del.; Patrick T. Shannon, Drexel Hill, Pa.

[73] Assignee: E. I. Du Pont de Nemours and Company, Wilmington, Del.

[21] Appl. No.: 939,567

[22] Filed: Sep. 3, 1992

Related U.S. Application Data

[63] Continuation of Ser. No. 641,991, Jan. 16, 1991, abandoned, which is a continuation of Ser. No. 275,189, Nov. 23, 1988, abandoned.

[51] Int. Cl.$^5$ .................. C12N 11/08; G01N 33/545; C08F 20/44; C07K 3/20
[52] U.S. Cl. .................................. 435/180; 435/803; 436/531; 525/329.1; 530/413; 530/815
[58] Field of Search ............... 435/174, 177, 180, 181, 435/803; 525/329.1; 436/531; 530/413, 815

[56] References Cited

U.S. PATENT DOCUMENTS

| | | | |
|---|---|---|---|
| 2,810,726 | 10/1959 | Howard | 260/296 |
| 4,371,612 | 2/1983 | Matsumoto et al. | 435/180 X |
| 4,486,549 | 12/1984 | Matsumoto et al. | 435/180 X |
| 4,705,753 | 11/1987 | Gregor et al. | 435/180 |

OTHER PUBLICATIONS

A. L. Endrey, "The Base-Catalyzed Transformation of Polyacrylonitrile," *Journal of Polymer Science: Polymer Chemistry Edition*, vol. 20, pp. 2105-2116 (1982).

Handa et al., "The Effect of Methlacrylate on the Activity of Glucoamylase Immobilization on Granular Polyacrylonitrile," *Biotechnology and Bioengineering*, vol. XXIV, pp. 1639-1652 (1982).

Okamoto et al., "Effect of Hydrogen Chloride on Thermal Degradation of Polyacrylonitrile," *J. Chem. Soc. Japan*, No. 4, pp. 566-570 (1983).

*Primary Examiner*—David M. Naff

[57] ABSTRACT

Polyacrylonitrile is chemically modified with HX (Cl, Br, I, CF$_3$SO$_3$H) to produce a polymer with readily replaceable X groups. The modified polyacrylonitrile is useful as an immobilization substrate for, e.g., proteins and in affinity chromatography

27 Claims, No Drawings

POLYACRYLONITRILE MODIFIED WITH HYDROGEN HALIDE FOR IMMOBILIZATION OF BIOLOGICAL SUBSTANCES

This is a continuation of application Ser. No. 07/641,991, filed Jan. 16, 1991, now abandoned, which is a continuation of application Ser. No. 07/275,189, filed Nov. 23, 1988, now abandoned.

BACKGROUND OF THE INVENTION

This application relates to chemically modified polyacrylonitrile (PAN) obtained by reaction of PAN with HX, to a corresponding method for modifying PAN and to the use of the modified PAN as an immobilization substrate, inter alia.

Polyacrylonitrile has been modified in various ways in the past. For example, A. L. Endrey, J. Poly. Sci., Poly. Chem. Ed. 20 2105 (1982) discusses the conversion cf polyacrylonitrile to a black form having the suggested structure:

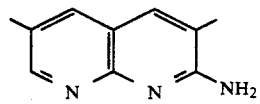

In addition to being black, it is hygroscopic, insoluble in all solvents, and has no nitrile groups.

M. Okamoto, T. Ogura, R. Ashihawa, and O. Ishizuka, Chem. Soc., Japan 566-570 (1983) found that polyacrylonitrile reacts very little with HCl below 220° C. Above this temperature, the nitrile groups are polymerized giving:

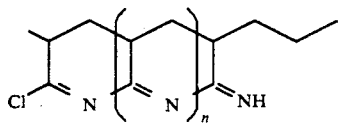

in which all nitrile groups have been polymerized and only a single Cl group is contained. The heat-treated polyacrylonitrile has been used to immobilize enzymes.

S. O. Bachurin et al, Doklady Ahademii Nauk, USSR 253 370-372 (1980) (English Translation) oxidized heat-treated polyacrylonitrile with HNO₃ and then absorbed hydrogenase on it. The binding is reversible.

K. Matsumoto et al, U.S. Pat. No. 4,486,549 (Dec. 4, 1984) (to Toyo Jozo Co.) reduced polyacrylonitrile with LiAlH₄ to produce some amine groups. This was used as a binding support for proteins.

Polyacrylonitrile has also been derivatized with an alcohol under the influence of HCl. The imidioester is then converted to an amidine:

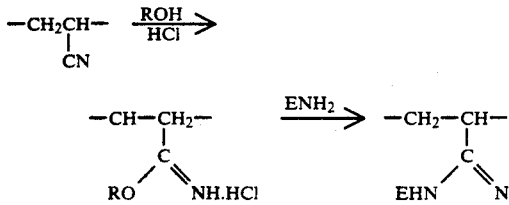

T. Handa, A. Hirose, S. Yoshida, H. Tsushia, Biotech. and Bioeng. 24 1639-1652 (1982) used the product to mobilize glucoamylase. A. Biondi, M. Pace, O. Brenna, and P. G. Pielta, Biochem. 61 171-174 (1976) coupled oxidase, glucose oxidase, and lactate dehydrogenase to alcoholated polyacrylonitrile.

In addition, U.S. Pat. No. 2,810,726 discloses the reaction of dinitriles, such as succinonitrile or glutaronitrile, with HX to produce compounds of the formula:

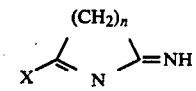

wherein X is Br or I and n is 2 or 3.

SUMMARY OF THE INVENTION

It is an object of this invention to provide chemically modified PAN having useful properties, e.g., for immobilization of biological materials, and also a process for preparing such a modified PAN. It is also an object of this invention to provide such substrates having biological materials immobilized thereon.

Upon further study of the specification and appended claims, further objects and advantages of this invention will become apparent to those skilled in the art.

These objects have been achieved in one aspect by providing modified polyacrylonitrile containing at least one unit of the structure

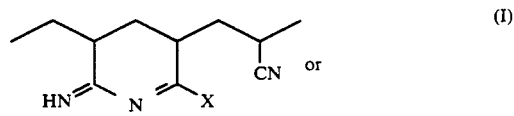

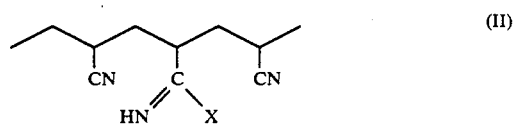

wherein X is Br, Cl, I or CF₃SO₃.

In another aspect, they have been achieved by providing modified polyacrylonitrile produced by reacting polyacrylonitrile with HX, wherein X is Cl, Br, I or CF₃SO₃. The invention also provides corresponding processes comprising reacting PAN with HX at a temperature less than about 115° C.

In still another aspect, these objects have been achieved by providing modified PAN having biological materials immobilized thereon, e.g., microorganisms, animal (e.g., mammalian) cells, proteins, nucleic acids (e.g., DNA), etc.

The structures of the products of all versions of the processes of this invention have the Formulae I and II given above. Polyacrylic structures (III)

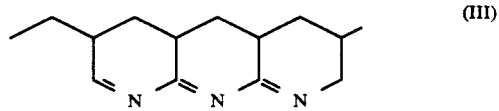

normally resulting from polyacrylonitrile reactions surprisingly do not form. The latter are known to be insoluble, highly colored or black, whereas the products of this invention are essentially colorless. In addition, the analytical data are inconsistent with Formula III.

The process of this invention for modifying PAN can be carried out in a solvent which dissolves the reactants (especially PAN) and is inert thereto (especially HX). Suitable solvents include sulfolane and butyroactones, sulfolane being preferred. Typically, the concentration of PAN in the solvent is 0.006 to 0.4 mole %, and the ratio of reactant HX to PAN is about 0.01 to 1.0, preferably 0.1 to 0.5 mole/mole of CN groups in the polyacrylonitrile. The amount of X which is incorporated into the polymer is primarily dependent upon its concentration in the reaction medium. An excess of HX can be used if desired, in which case the amount of X incorporated into the polymer can be controlled by temperature and contact time.

The reaction typically is conducted temperatures of $0°$-$115°$ C. preferably $20°$-$110°$ C., most preferably $20°$-$30°$ C. The reaction can be performed at room temperature. Typical reaction times are on the order of 1 to 4 hours, shorter and longer times also being useful.

The reaction is carried out under anhydrous conditions. Water reacts with the —N=CS— group of the modified PAN producing —NH—CO—. The latter group will not bind linkers or biological materials. As a result, a tolerable upper limit of water is about 0.001 moles/mol of HX.

The process according to the invention preferably is performed in a single step, i.e., reacting PAN with HX.

The reaction is essentially applicable to any type of PAN. Polyacrylonitrile copolymers can also be utilized, e.g., those wherein the comonomer is one or more of methylacrylate, methylvinylpyridine, styrene, etc. Additional copolymers of PAN which are suitable for the process of this invention include copolymers made with acrylonitrile and one or more of the following compounds:

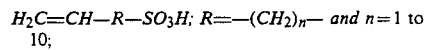

$H_2C=CH—R—SO_3H$; $R=—(CH_2)_n—$ and $n=1$ to 10;

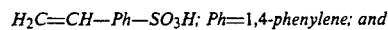

$H_2C=CH—Ph—SO_3H$; $Ph=1,4$-phenylene; and

$H_2C=CH—CO—NH—CH_2CH(CH_3)CH_2SO_3H$

The mole percent of comonomer that can be contained in the copolymers can range from 1 to 50%. Such copolymers as described above are prepared fully conventionally, e.g., by processes disclosed in "Preparation Methods of Polymer Chemistry," Sorenson & Campbell, *Interscience*, 1961, pp. 210-211.

The product of this process of this invention can be worked up fully conventionally For example, the product contained in sulfolane can be precipitated with the addition of an inert solvent, such as methylene chloride, recovered by filtration, washed with additional sulfolane and dried by purging with nitrogen under mild heat.

In an alternative embodiment for preparing the chemically modified PAN of this invention, the dry polymer itself can be reacted with any of the HX's in the absence of a solvent. For this embodiment, the same starting material PAN's are fully applicable. The dry process is typically carried out at elevated temperatures and pressures. For example, reaction of PAN with HBr at $100°$ C. under normal pressure produces a product containing only about 3.4% bromine. As a result, increased pressures are greatly preferred, e.g., typically in the range of 2-20 atmospheres, greater pressures also being applicable. At elevated pressures, suitable reaction temperatures are in the range of $20°$-$100°$ C., preferably between $20°$-$50°$ C. and most preferably $20°$-$30°$ C. When using HBr as HX, the maximum upper temperature which can be tolerated in the dry process is about $100°$ C.-$115°$ C. Similarly, the upper temperature limit for the other HX's is about $115°$ C.

The dry process must also be carried out under essentially anhydrous conditions, the upper tolerable limit on water content being typically 0.001 mole per mole of HX.

The reaction of HX with PAN can also be performed by suspending PAN in a non-solvent. Non-solvents which are suitable for the process include $C_5$ to $C_{20}$ branched and straight chain hydrocarbons, $C_5$ to $C_{12}$ cyclic hydrocarbon, aromatic hydrocarbons such as benzene, or toluene, and chlorocarbons such as $CH_2Cl_2$, $CHCl_3$, $CCl_4$ and $C_6H_5Cl$. The general reaction conditions for the PAN suspended in a non-solvent are the same as for the solvent or dry process.

The work-up from the dry process using no solvent or using a non-dissolving liquid medium is also fully conventional, e.g., can involve recovery by filtration followed by rinsing with fresh solvent and drying as described above.

Commercial PAN's which can be used in the processes of this invention include: Orlon ® 43, 44 and 46 (as tow, woven and non-woven); DuPont's A-7 (a powder form of PAN); acrylonitrile/butadiene copolymers; and acrylonitrile/butadiene/styrene copolymers, inter alia.

It is also possible to obtain salt structures analogous to those discussed in col. 6 of U.S. Pat. No. 2,810,726. These salt structures can be converted to other salts by simple exchange reactions. However, the free base form is the preferred structure for attaching linkers and proteins. In another alternative, it is also possible to prepare modified PAN's having more than one type of X by simply reacting compatible mixtures of two different HX's with a given PAN or sequentially performing HX reactions. For a given reaction of this invention, the relative amounts of Formula I and/or Formula II structures which will be prepared can be readily determined by conventional diagnostic procedure, where desired.

The percentage of X which can be incorporated into the products of this invention by the dry or non-solvent processes can also be routinely controlled primarily by correspondingly varying the amount of HX present. Gaseous diluents can be used along with the HX in the dry system. However, additional inert co-ingredients in the gaseous phase are not necessary. In addition, of course, the percentage of X can be increased in all cases by increasing the time of reaction, i.e., the extent of completion of reaction. The theoretical upper limit on the percentage of X in the resultant product is ½ the original number of CN groups present in the PAN. Typically, the most useful products will have a number of X groups equivalent to about at least 5%, preferably about at least 20%, most preferably about at least 30%, and especially about at least 40% of the number of CN groups in the starting PAN.

When HX is HBr, some of the resultant modified PAN products are partially or highly water-soluble. This result is advantageous for all HX's since water solubility is a desired feature for coatings and for product isolation. However, as mentioned above, the products of this invention react slowly with water. As a result, all operations performed in the presence of water must be done at low temperatures and contact times must be kept to a minimum.

The water soluble products can be precipitated by changing the ionic strength of the product mixture. The acids, bases and salts that can be added to achieve the ionic strengths necessary to precipitate the products of this invention include mineral acids such as sulfuric acid, mineral bases such as sodium hydroxide, and salts such as sodium chloride and sodium sulfate.

The products of this invention are useful for immobilization of biological substances including microorganisms, cells, affinity chromatography ligands, proteins, etc., e.g., enzymes, antibodies (monoclonal and polyclonal), antigens, factors, etc. Such immobilization products can be fully prepared using conventional immobilization procedures and conditions, e.g., as thoroughly disclosed in,e.g., U.S. Pat. No. 4,539,294; U.S. Pat. No. 4,582,875; U.S. Pat. No. 4,252,653; U.S. Pat. No. 4,572,897; U.S. Pat. No. 4,647,280; *Affinity Chromatography*, by W. H. Scouten, Wiley, N.Y., (1981); *Affinity Chromatography and Biological Recognition*, I. M. Chaiken, M. Wilchek, I. Parikh (eds.), Academic Press, N.Y., (1983); and *Methods of Enzymology* Vol. 34, W. B. Jakoby and M. Wilchek (eds.), Academic Press, N.Y. (1974).

Suitable proteins for affinity chromatography include lectins (e.g., concavalin A); receptor proteins (e.g., insulin receptor); haptens; heparin (for isolation of blood clotting factors); and Protein A and Protein G (for isolation of IgG). Other suitable ligands include cofactors (e.g., NAD, AMP, cAMP, biotin, FMN); sugars, polysaccharides and their derivatives (e.g., N-acetylglucosamine, thioglycosides, wheat germ agglutinin); dyes and chemical compounds which demonstrate affinity for specific proteins or classes of proteins (e.g., blue dextran, Cibacron blue $F_3$G-A, analine); metals and metal chelators (e.g., thiols, calmodulin); and thiol reactive compounds (e.g., 2-mercaptoethanol).

The literature contains a variety of references on the immobilization of whole cells. Examples include mouse spleen cells and bacterial cells. Suitable affinity chromatography ligands which can be immobilized are disclosed in the above-mentioned references concerning immobilization procedures. See also *Methods in Enzymology*. p. 3; W. B. Jakoby and M. Wilchek (eds.), Academic Press, N.Y. (1974).

The products of this invention are highly advantageous for this use as support matrices for such immobilizations, inter alia, in view of their low cost, hydrophilicity and capability of being configured into a wide variety of forms, such as fibers, spun fibers, pellicular beads, films, coatings, etc. In addition, they can be provided in the form of amorphous powders and surface derivatized PAN (dry process above as applied, e.g., to Orlon ®.) Moreover, the resultant immobilized biological and other entities remain viable and suitable for their intended use. Attachment of a biomolecule to a substrate of this invention, for example, does not alter the structural integrity of its polymeric backbone or that of PAN either.

The materials are also preferred as immobilization substrates because they have highly controlled and predictive derivatization chemistries as discussed above, and are stable under aqueous conditions, in the pH range of 2-10 and at varying ionic strengths Typically, immobilization of the biological and other entities to a substrate is carried out via an intermediate spacer. The nature of the spacer is not critical. Wide varieties of structures and lengths are known and these can all be used in conjunction with this invention using fully conventional conditions and procedures as disclosed in, for example, the literature cited above, e.g., *Affinity Chromatography*, p. 38 and 42, W. H. Scouten, Wiley, N.Y. (1981) and J. Porath, in *Methods in Enzymology*, Vol. 34, p. 13, W. Jakoby and M. Wilchek (eds.), Academic Press, N.Y. (1974). It is also possible to attach a material such as a protein directly to the substrate of this invention without a spacer, again using fully conventional considerations and procedures. Similarly, the chemical entity by which attachment is made is not critical. Typically, this will be an amino group but other nucleophiles, for example, can be used, e.g., alcohols, thiols, hydrazines, etc.

The substrates of this invention are particularly good candidates for use in affinity chromatography, especially for medical applications. They can be used for this purpose analogously to other conventional substrates, e.g., as discussed in the literature cited above as well as *Affinity Chromatography*, p. 38 and 42, W. H. scouten, Wiley, N.Y. (1981) and J. Porath, in *Methods in Enzymology*, Vol. 34, p. 13, W. Jakoby and M. Wilchek (eds.), Academic Press, N.Y. (1974). They are particularly applicable to affinity chromatography involving purification and separation of IgG antibodies using immobilized Protein A and Protein G, apoprotein B containing lipoprotein particles (LDL, VLDL) using immobilized antibodies where low nonspecific protein binding and low complement activation is desired.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications cited above and below are hereby incorporated by reference.

Percent X contents are calculated using:

$$\% X = [(wt.\ X)/(wt.\ H_2C=CHCN + wt.\ HX)\pi \times 100$$

EXAMPLES 1-3

Preparation of Brominated Polyacrylonitrile

Gaseous hydrogen bromide (115 ml, 4.7 mmoles) was added to a solution consisting of 1 g. of dry polyacrylonitrile (19 mmole CN groups) in 30 ml. of dry sulfolane at room temperature. After two hours reaction at 25° C., the polymer was precipitated by adding the sulfolane solution to an excess of methylene chloride in a blender. In a similar experiment, the amount of hydrogen bromide was increased to 2) 230 ml (9.5 moles) and 3) 460 ml (19 moles). The products gave the following analysis:

1) C, 61.74%; H, 6.22%; N, 23.71%; Br, 8.23%
2) C, 50.16%; H, 5.95%; N, 18.86%; Br, 23.98%
3) C, 38.47%; H, 2.46%; N, 13.02%; Br, 44.00%.

Infrared analysis of the products showed absorption at 3400 cm$^{-1}$ and 2800 cm$^{-1}$ for N—H; 1620 cm$^{-1}$ and 1570 cm$^{-1}$ for C=N; and 2240 cm$^{-1}$ for CN. The infrared data are consistent with the following heterocyclic structure:

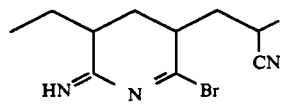

EXAMPLE 4

Preparation of Chlorinated Polyacrylonitrile

Excess dry HCl was passed into a solution consisting of 5 g. of polyacrylonitrile in 100 ml of sulfolane for one hour at 25°–30° C. The polymer was precipitated by adding the sulfolane solution to an excess of methylene chloride and recovered by filtration. The polymer was washed with methylene chloride and recovered by filtration. The polymer was washed with methylene chloride and dried. The recovered product weighed 5 g. Elemental analysis of the product gave 5.3% chlorine.

Infrared analysis of the product showed absorption at 3400 cm$^{-1}$ and 2600 cm$^{-1}$ for N—H; and 1670 cm$^{-1}$ for C=N. The presence of only one peak in the C=N region is consistent with the following structure:

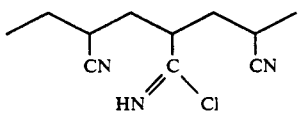

EXAMPLE 5

Preparation of Iodinated Polyacrylonitrile

Dry hydrogen iodide (6 g, from P$_2$O$_5$ and aqueous HI) was bubbled into a solution consisting of 5 g. of polyacrylonitrile in 200 ml. of sulfolane at 25° C. The polymer was precipitated by adding the sulfolane solution to an excess of methylene chloride. The product was recovered by filtration and dried.

Infrared analysis of the product showed absorption at 3200 cm$^{-1}$ for NH; 2240 cm$^{-1}$ for CN; 1670 cm$^{-1}$ for linear C=N and 1590 cm$^{-1}$ for ring C=N. The product is a mixture containing imino iodide (analogous to Example 4) and the nitrogen heterocycle (analogous to Example 1).

EXAMPLE 6

Reaction of Polyacrylonitrile with CF$_3$SO$_3$H

Trifluoromethanesulfonic acid (5 g., 33 mmoles) was added to 5 g. of polyacrylonitrile dissolved in 100 ml of sulfolane at 25° C. After one hour the product was precipitated by adding the sulfolane solution to an excess of methylene chloride. The product was recovered by filtration and dried.

Elemental analysis of the product gave 6.21% fluorine.

Infrared analysis of the product showed absorption at 3400–3000 cm$^{-1}$ for NH; and 1665 cm$^{-1}$ for C=N. The analysis is consistent with the following structure:

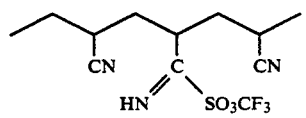

EXAMPLE 7

Reaction of Solid Polyacrylonitrile with HBr

Dry Orlon T-43 fiber [96% polyacrylonitrile/4% styrene sulfonic acid, Na+ salt] (10 g.) was placed into a 5 ml Hasteloy pressure vessel with 12 g. of HBr gas at 25° C. (with solvent pressures are somewhat lower) and about 200 Psig for 20 hours. A yellow-orange matte of fibers reed weighing 18.8 g.

Elemental analysis of the product gave 34.35% bromine.

The product was mostly soluble in water and precipitated when either aqueous sodium hydroxide or acetic acid as added.

EXAMPLE 8

Reaction of Solid Polyacrylonitrile with HCl

Dry Orlon T-43 fiber (10.4 g.) was placed into a 75 ml Hasteloy Pressure vessel with 20 g. of dry HCl at 21°–28° C. and at 200 psig for 20 hours. The product became lumpy and was soluble in water. The polymer was precipitate from the aqueous solution with either aqueous ba or acetic acid.

Elemental analysis of the product gave 33.26% chlorine.

EXAMPLE 9

Reaction of Orlon-44 with HBr

A 360 ml Hasteloy pressure vessel was charged with 12.3 g Orlon-44 [89.8% acrylonitrile, 6% methylacrylate, 4.2% methylvinylpyridine] fibers and 6 g dry HBr. After two hours at 25° C. and about 200 psig, the vessel was vented. The product (15.2 g) contained 4.54% bromine.

EXAMPLE 10

Reaction of Orlon-42 with HBr

A 240 ml Hasteloy pressure vessel was charged with 11.8 g Orlon-42 [94% acrylonitrile, 6% methylacrylate] and 5 g HBr. After two hours at 25° C. and about 200 psig, the vessel was vented. The product contained 14.8% bromine.

EXAMPLE 11

Immobilization Anti-apoprotein B monoclonal antibody

Linker Attachment

To 0.5 g of HBr activated polyacrylonitrile (PAN) powder, 7.34% Br was added 5 ml dry dioxane. After a homogeneous suspension was obtained, 10 ml of 25% 1,6-diaminohexane (w/v) in dioxane was added and the reaction mixture stirred for 7 days at room temperature using gentle agitation. The yellow solid was washed with dioxane, 0.1M phosphate buffer (pH 7), and distilled water to ensure complete removal of unreacted amine. After briefly rinsing with 0.1 m NaOH followed by distilled water, 10 ml of 1,4-butanedioldiglycidyl ether was added. The reaction mixture was maintained as a suspension by agitation for 24 hours at room temperature. The solid was rinsed with distilled water and copious amounts of ethanol and air dried. The epoxide content of the solid was 200-500 μmol/g by thiosulfate titration.

Protein Immobilization

The dry powder containing epoxide linker was hydrated by suspending in 0.1M phosphate buffer (pH 7) overnight. After rinsing the solid with distilled water, 2 volumes of anti-apoprotein B monoclonal antibody dissolved in 0.1M NaHCO3(pH 8.2) at a final concentration of 2-6 mg/ml was added and the suspension maintained by gentle agitation for 24 hours. The typical immobilization yields were 2-5 mg protein/g polymer. The retention of antibody activity was determined by its ability to selectively bind low density lipoprotein (LDL) from human plasma.

EXAMPLE 12

CF3SO3 - activated PAN

Linker attachment was carried out as described in Example 11. Anti-apoprotein B monoclonal antibody was attached to linker derivatized material as described in Example 11. Immobilization yield was 1.9 mg bound/g support. Assay of monoclonal activity was determined as described above.

EXAMPLE 13

Antibody Immobilization to Orlon Fiber 1 g of activated Orlon fiber (6.9% Br) was rinsed with ice cold phosphate buffered saline (pH 7.2). 10 ml of apoprotein B monoclonal antibody dissolved in 0.1M phosphate buffer (pH 8.3) was added to the fiber. Mixing was maintained by continually recirculating the solution through the fiber for 24 hours. Typical immobilization yields were 5-8 mg/g.

EXAMPLE 14

Protein A Immobilization to Orlon Fiber 1 g of activated Orlon fiber (6.9% Br) was rinsed with ice cold phosphate buffered saline (pH 7.2). 10 ml of *Staphylococcus aureus* derived Protein A dissolved in 0.1M phosphate buffer (pH 8.3) was added to the fiber. Mixing was maintained by continually recirculating the solution through the fiber for 24 hours. Typical immobilization yields were 1-2.5 mg/g. Immobilized Protein A activity was determined by its ability to bind human IgG.

The preceding examples can be repeated with similar success by substituting the generically or specifically described reactants and/or operating conditions of this invention for those used in the preceding examples From the foregoing description, one skilled in the art can easily ascertain the essential characteristics of this invention, and without departing from the spirit and scope thereof, can make various changes and modifications of the invention to adapt it to various usages and conditions.

What is claimed is:

1. An immobilized biological substance comprising a biological substance immobilized on a modified polyacrylonitrile containing at least one unit of the structure

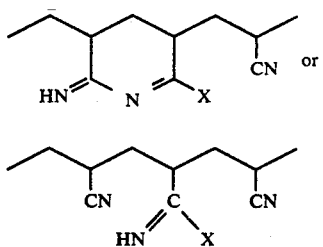

wherein X is Br, Cl, I or CF3SO3, and said biological substance is selected from the group consisting of microorganisms, animal cells, nucleic acids, enzymes, monoclonal antibodies, polyclonal antibodies, blood clotting factors, cofactors, sugars, lectins, receptor proteins, haptens, and heparin.

2. The immobilized biological substance of claim 1 wherein the polyacrylonitrile structure is of Formula I.

3. The immobilized biological substance of claim 1 wherein the polyacrylonitrile structure is of Formula II.

4. The immobilized biological substance of claim 1, wherein the number of X groups in the modified polyacrylonitrile is about at least 20% of the number of CN groups in the polyacrylonitrile before modification.

5. The immobilized biological substance of claim 1, wherein X is Br.

6. The immobilized biological substance of claim 1, wherein X is Cl.

7. The immobilized biological substance of claim 1, wherein X is I.

8. The immobilized biological substance of claim 1, wherein X is CF3SO3.

9. The immobilized biological substance of claim 1, wherein the modified polyacrylonitrile contains at least two of Cl, Br, I or CF3SO3.

10. The immobilized biological substance of claim 1 wherein said biological substance is a bloodclotting factor.

11. The immobilized biological substance of claim 1 wherein said biological substance is an antibody.

12. The immobilized biological substance of claim 1 wherein said biological substance is a lectin.

13. The immobilized biological substance of claim 1 wherein said biological substance is a receptor protein.

14. The immobilized biological substance of claim 1 wherein said biological substance is a hapten.

15. The immobilized biological substance of claim 1 wherein said biological substance is a heparin.

16. A process for preparing a biological substance immobilized on a modified polyacrylonitrile containing at least one unit of the structure

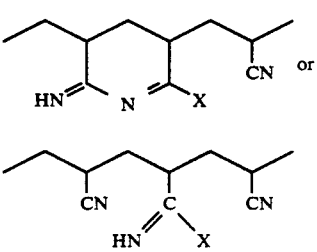

wherein X is Br, Cl, I or CF3SO3, comprising reacting a polyacrylonitrile with HX wherein X is said X at a temperature less than 115° C. in a solvent for the polyacrylonitrile under anhydrous conditions modified polyacrylonitrile and immobilizing a biological substance thereon.

17. A process of claim 15, wherein the reaction temperature is 20°-110° C.

18. A process of claim 17, wherein the solvent is sulfolane.

19. A process for preparing a biological substance immobilized on a modified polyacrylonitrile containing at least one unit of the structure

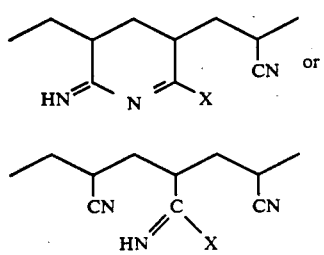

wherein X is Br, Cl, I or CF$_3$SO$_3$ comprising reacting a polyacrylonitrile in solid form with HX wherein X is said X at a temperature less than 115° C. at a pressure greater than 1 atm under anhydrous conditions to produce said modified polyacrylonitrile and immobilizing a biological substance thereon.

20. A process of claim 19, wherein the reaction pressure is 2-20 atms and the reaction temperature is 20°-110° C.

21. An immobilized ligand useful for affinity chromatography comprising a ligand immobilized on a modified polyacryonitrile containing at least one unit of the structure

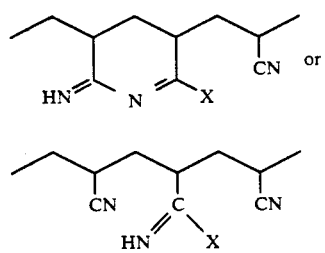

wherein X is Br, Cl, I or CF$_3$SO$_3$.

22. The immobilized ligand of claim 2, wherein the ligand is selected from the group consisting of dyes, metals, metal chelators, cofactors, sugars, and compounds that react with a thiol compound.

23. The immobilized ligand of claim 22 wherein the ligand is a cofactor.

24. A method for carrying out affinity chromatography comprising immobilizing a ligand on a modified polyacrylonitrile containing at least one unit of the structure

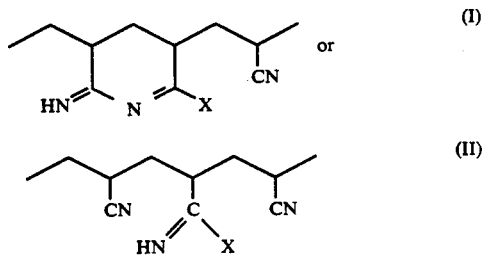

wherein X is Br, Cl, I or CF$_3$SO$_3$, and using the immobilized ligand to bind a substance thereto.

25. Modified polyacrylonitrile produced by reacting a polyacrylonitrile with at least one HX at a temperature less than 115° C. wherein X is CF$_3$SO$_3$.

26. Modified polyacrylonitrile containing at least one unit of the structure

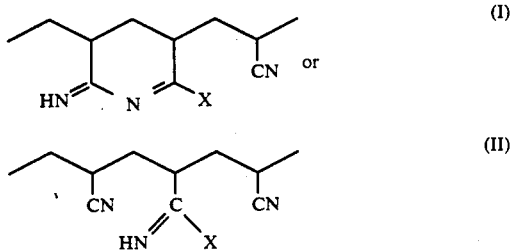

wherein X is CF$_3$SO$_3$.

27. A process for preparing modified polyacrylonitrile containing at least one unit of the structure

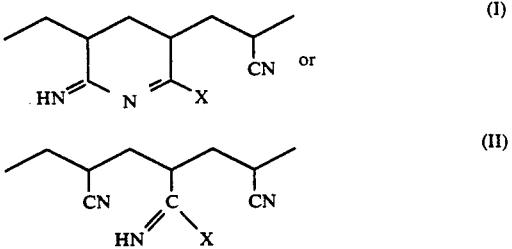

wherein X is CF$_3$SO$_3$, comprising reacting a polyacrylonitrile with HX at a temperature less than 115° C.

* * * * *